(12) United States Patent
LaBombard

(10) Patent No.: US 9,408,594 B2
(45) Date of Patent: Aug. 9, 2016

(54) SELF CLOSING TISSUE FASTENER

(75) Inventor: Denis LaBombard, Georgetown, MA (US)

(73) Assignee: Aponos Medical Corporation, Kingston, NH (US)

( * ) Notice: Subject to any disclaimer, the term of this patent is extended or adjusted under 35 U.S.C. 154(b) by 492 days.

(21) Appl. No.: 11/728,569

(22) Filed: Mar. 26, 2007

(65) Prior Publication Data

US 2007/0225762 A1 Sep. 27, 2007

Related U.S. Application Data

(60) Provisional application No. 60/785,830, filed on Mar. 25, 2006.

(51) Int. Cl.
*A61B 17/06* (2006.01)
*A61B 17/00* (2006.01)
(Continued)

(52) U.S. Cl.
CPC ............ *A61B 17/0057* (2013.01); *A61B 17/068* (2013.01); *A61B 17/0644* (2013.01); *A61B 2017/00579* (2013.01); *A61B 2017/00592* (2013.01); *A61B 2017/00623* (2013.01); *A61B 2017/00668* (2013.01); *A61B 2017/00862* (2013.01); *A61B 2017/00889* (2013.01); *A61B 2017/00893* (2013.01);
(Continued)

(58) Field of Classification Search
CPC ............ A61B 17/0644; A61B 17/064; A61B 17/0057; A61B 2017/0641; A61B 2017/0645
USPC .................................... 606/21–219; 623/1.23
See application file for complete search history.

(56) References Cited

U.S. PATENT DOCUMENTS 3,266,059 A 8/1966 Stelle
3,598,125 A 8/1971 Cogley
(Continued)

FOREIGN PATENT DOCUMENTS

DE 197 11 673 A1 10/1998
DE 10 2004 01529 10/2004
(Continued)

OTHER PUBLICATIONS

International Search Report and Written Opinion mailed Aug. 30, 2007 from International Application No. PCT/US2007/007396 filed Mar. 26, 2007.

(Continued)

*Primary Examiner* — Alexander Orkin
(74) *Attorney, Agent, or Firm* — Hamilton, Brook, Smith & Reynolds, P.C.

(57) ABSTRACT

A self-closing tissue fastener for use in wound closure and surgery has, in an annular configuration, a central ring; tissue-piercing spines projecting from a first side of the ring; and stabilizing members projecting from a second side of the ring. The fastener can be carried on the inside of a tube, where it is stable without additional restraint, as well as on the outside of a tube or mandrel. The device can be compressed from a planar state, as fabricated, to the annular state by compressing the stabilizers (or, if they are on the outside in the planar form, the barbs). Unlike present devices, which are not as stable in the annular state, the inventive device and an applicator therefore provide an open channel to a site of surgery, for passage of endoscopes or various endoscopic and similar instruments. In particular, the fastener can be delivered under endoscopic monitoring.

21 Claims, 11 Drawing Sheets

(51) Int. Cl.
*A61B 17/064* (2006.01)
*A61B 17/068* (2006.01)

(52) U.S. Cl.
CPC *A61B 2017/0641* (2013.01); *A61B 2017/0645* (2013.01); *A61B 2017/0647* (2013.01)

(56) References Cited

U.S. PATENT DOCUMENTS

| | | | |
|---|---|---|---|
| 3,613,683 | A | 10/1971 | Kees, Jr. et al. |
| 3,954,108 | A | 5/1976 | Davis |
| 4,217,902 | A | 8/1980 | March |
| 4,735,194 | A | 4/1988 | Stiegmann |
| 4,791,707 | A | 12/1988 | Tucker |
| 4,832,027 | A | 5/1989 | Utz |
| 5,026,379 | A | 6/1991 | Yoon |
| 5,035,692 | A | 7/1991 | Lyon et al. |
| 5,174,276 | A | 12/1992 | Crockard |
| 5,190,542 | A | 3/1993 | Nakao et al. |
| 5,201,908 | A | 4/1993 | Jones |
| 5,217,001 | A | 6/1993 | Nakao et al. |
| 5,334,209 | A | 8/1994 | Yoon |
| 5,381,782 | A | 1/1995 | DeLaRama et al. |
| 5,386,817 | A | 2/1995 | Jones |
| 5,569,274 | A | 10/1996 | Rapacki et al. |
| 5,651,788 | A | 7/1997 | Fleischer et al. |
| 5,695,448 | A | 12/1997 | Kimura et al. |
| 5,972,002 | A | 10/1999 | Bark et al. |
| 6,059,719 | A | 5/2000 | Yamamoto et al. |
| 6,071,233 | A | 6/2000 | Ishikawa et al. |
| 6,152,937 | A * | 11/2000 | Peterson et al. .............. 606/153 |
| 6,196,966 | B1 | 3/2001 | Kerin et al. |
| 6,197,042 | B1 * | 3/2001 | Ginn et al. .................... 606/213 |
| 6,293,909 | B1 | 9/2001 | Chu et al. |
| 6,306,081 | B1 | 10/2001 | Ishikawa et al. |
| 6,428,548 | B1 | 8/2002 | Durgin et al. |
| 6,450,948 | B1 | 9/2002 | Matsuura et al. |
| 6,520,974 | B2 | 2/2003 | Tanner et al. |
| 6,569,085 | B2 | 5/2003 | Kortenbach et al. |
| 6,582,452 | B2 | 6/2003 | Coleman et al. |
| 6,602,263 | B1 * | 8/2003 | Swanson et al. .............. 606/153 |
| 6,669,708 | B1 | 12/2003 | Nissenbaum et al. |
| 6,689,130 | B2 | 2/2004 | Arai et al. |
| 6,699,180 | B2 | 3/2004 | Kobayashi |
| 6,726,704 | B1 * | 4/2004 | Loshakove et al. .......... 606/213 |
| 6,849,078 | B2 | 2/2005 | Durgin et al. |
| 6,911,032 | B2 | 6/2005 | Jugenheimer et al. |
| 6,926,731 | B2 | 8/2005 | Coleman et al. |
| 6,974,411 | B2 | 12/2005 | Belson |
| 7,001,398 | B2 | 2/2006 | Carley et al. |
| 7,056,284 | B2 | 6/2006 | Martone et al. |
| 7,059,508 | B2 | 6/2006 | Shelton, IV et al. |
| 7,189,247 | B1 | 3/2007 | Zirps et al. |
| 7,204,804 | B2 | 4/2007 | Zirps et al. |
| 7,575,548 | B2 | 8/2009 | Takemoto et al. |
| 7,588,580 | B2 | 9/2009 | Okada |
| 8,182,422 | B2 | 5/2012 | Bayer et al. |
| 8,313,496 | B2 | 11/2012 | Sauer et al. |
| 8,920,311 | B2 | 12/2014 | LaBombard |
| 2001/0053909 | A1 | 12/2001 | Nakada et al. |
| 2002/0055668 | A1 | 5/2002 | Pauker |
| 2002/0082641 | A1 * | 6/2002 | Ginn et al. .................... 606/213 |
| 2002/0133150 | A1 | 9/2002 | Whayne |
| 2002/0188318 | A1 | 12/2002 | Carley et al. |
| 2003/0153932 | A1 | 8/2003 | Spence et al. |
| 2003/0158578 | A1 | 8/2003 | Pantages et al. |
| 2004/0068279 | A1 | 4/2004 | Hindrichs et al. |
| 2004/0087981 | A1 | 5/2004 | Berube et al. |
| 2004/0097982 | A1 | 5/2004 | Jugenheimer et al. |
| 2004/0210111 | A1 | 10/2004 | Okada |
| 2004/0230095 | A1 | 11/2004 | Stefanchik et al. |
| 2005/0075538 | A1 | 4/2005 | Banik et al. |
| 2005/0107667 | A1 | 5/2005 | Danitz et al. |
| 2005/0283188 | A1 * | 12/2005 | Loshakove et al. .......... 606/213 |
| 2006/0058582 | A1 | 3/2006 | Maahs et al. |
| 2006/0069304 | A1 | 3/2006 | Takemoto et al. |
| 2006/0135989 | A1 | 6/2006 | Carley et al. |
| 2007/0197862 | A1 | 8/2007 | Deviere et al. |
| 2007/0270752 | A1 | 11/2007 | LaBombard |
| 2010/0038403 | A1 | 2/2010 | D'Arcangelo |
| 2010/0048988 | A1 | 2/2010 | Pastorelli et al. |
| 2010/0069933 | A1 | 3/2010 | D'Arcangelo et al. |
| 2010/0125164 | A1 | 5/2010 | LaBombard |
| 2010/0133320 | A1 | 6/2010 | Bilotti et al. |
| 2015/0230782 | A1 | 8/2015 | LaBombard |

FOREIGN PATENT DOCUMENTS

| | | |
|---|---|---|
| EP | 1 143 861 B1 | 7/2011 |
| EP | 2 263 572 B1 | 8/2014 |
| WO | WO 03/071955 | 9/2003 |
| WO | WO 2004/103430 A2 | 12/2004 |
| WO | WO 2010/059200 A1 | 5/2010 |

OTHER PUBLICATIONS

International Search Report "Multifunctional Instrument Introducer," mailed Nov. 6, 2007 from International Application No. PCT/US2007/012049 filed May 18, 2007.

Written Opinion of the International Searching Authority "Multifunctional Instrument Introducer," mailed Nov. 6, 2007 from International Application No. PCT/US2007/012049 filed May 18, 2007.

International Search Report in International Application No. PCT/US2009/006164 "Adapter for Attaching Devices to Endoscopes," mailed Mar. 5, 2010.

International Preliminary Report on Patentability in International Application No. PCT PCT/US2009/006164 "Adapter for Attaching Devices to Endoscopes," mailed May 24, 2011.

ASGE/SAGES Working Group on Natural Orifice Translumenal Endoscopic Surgery, *Gastrointest Endosc*, 63(2):199-203 (2006).

Cotton, P. B., "Interventional Gastroenterology (Endoscopy) at the Crossroads: A Plea for Restructuring in Digestive Diseases," *Gastroenterology*, 107:294-299 (1994).

Desilets, D., et al., "Gastric closure in NOTES using a novel, over-the-scope nitinol clip—A survival study in an animal model", International NOSCAR Conference on NOTES (4th). Boston, MA. Jul. 9-Jul. 11, 2009, 1 page.

Desilets, D., et al., "Gastrotomy closure with the lock-it system and the Padlock-G clip: a survival study in a porcine model", *J. Laparoendosc. Adv. Surg. Tech. A.*, 20(8):671-676 (2010). PubMed Abstract, available at: http://www.ncbi.nlm.nih.gov/pubmed/20687850, 1 page.

Fritscher-Ravens, A., et al., "Transgastric Gastropexy and Hiatal Hernia Repair for GERD Under EUS Control: A Porcine Model," *Gastrointest Endosc*, 59(1):89-95 (2004).

Guarner-Argente, C., et al., "Yes, we can: reliable colonic closure with the Padlock-G clip in a survival porcine study (with video)", *Gastrointestinal Endoscopy*, 72(4):841-844 (2010).

Jagannath, S. B. et al., "Peroral Transgastric Endoscopic Ligation of Fallopian Tubes with Long-Term Survival in a Procine Model," *Gastrointest Endos*, 61(3):449-453 (2005).

Modlin, I. M., "Perspectives and Reflections on Integrated Digestive Surgery," *Best Practice & Res Clin Gastroenterol*, 16(6):885-914 (2002).

Ponsky, J. L., "Gastroenterologists as Surgeons What They Need to Know", *Gastrointest Endosc*, 61(3):454 (2005).

Romanelli, J.R., et al., "Natural orifice translumenal endoscopic surgery gastrotomy closure in porcine explants with the Padlock-G clip using the Lock-It system", *Endoscopy*, 42:306-310 (2010).

Vitale, G. C., et al., "The Advancing Art and Science of Endoscopy", *Amer J. Surg*, 190:228-233 (2005).

* cited by examiner

SELF CLOSING TISSUE FASTENER

PRIORITY

This application claims the benefit of the priority of U.S. provisional application 60/785,830, filed Mar. 25, 2006, which is hereby incorporated in its entirety by reference where permitted.

FIELD OF THE INVENTION

The present invention relates generally to medical apparatus and methods for securing tissue. More particularly, the present invention describes a unique self closing tissue fastener, which is a device for securing or closing of surgically altered tissue, where the device is itself self closing in nature. The device comprises a central ring to which both tissue-piercing members and stabilizing members are affixed. The stabilizing members allow the device to be stored in its activated state on the inside of a tube. As a result, the fastener delivery apparatus can provide an unobstructed, preferably sealed, working access channel through which other surgical instruments, devices and apparatus, for diagnosis or for the control, closure or manipulation of tissue, may be delivered to the surgical site. In particular, a fastener can be delivered to a site under endoscopic observation.

BACKGROUND OF THE INVENTION

There are many techniques employed to close, secure or lock tissue into a preferred configuration. These techniques include suturing, stapling, taping and the like. Selection of which technique to employ depends upon the type of tissue being repaired, the tissue location, and the required strength of the repair.

The following U.S patents are representative of the state of the art in the general field of tissue fastener, staple, clip fastener and closure delivery apparatus technology and designs, which now are commonly used in numerous surgical procedures to close or lock tissue apertures, incisions, and the like:
U.S. Pat. No. 7,112,214 Peterson et al.; U.S. Pat. No. 7,001,398 Carley et al; U.S. Pat. No. 7 6,926,731 Coleman et al; U.S. Pat. No. 6,746,460, Gannoe et al; U.S. Pat. No. 6,623,510, Carley et al; U.S. Pat. No. 5,667,527, Cook; U.S. Pat. No. 6,149,658, Remiszewski et al; U.S. Pat. No. 6,491,707 Makower at al; U.S. Pat. No. 6,884,248 Bolduc et al; U.S. Pat. No. 6,572,587 Lerman et al; U.S. Pat. No. 5,772,668 Summers et al; and U.S. Pat. No. 6,913,607 Ainsworth et al.

Many conventional surgical fasteners have been in the form of ordinary metal staples, which are bent by the delivery apparatus to hook together body tissue. Typically, conventional staples comprise a pair of legs joined together at one end by a crown. The crown may be a straight member connecting the legs or may form an apex. Moreover, the legs may extend substantially perpendicular from the crown or at some angle. Irrespective of the particular configuration, however, conventional staples are designed so that they may be deformed to hold body tissue.

Accordingly, the stapler applicators have conventionally embodied structure functioning to project the conventional staple into tissue as well as to deform the staple so that it is retained against the tissue. Such applicators as described by U.S. Pat. No. 6,446,854, Remiszewski et al., include an anvil cooperating with means to eject the conventional staple from the applicator. In some applications, access to the body tissue from two opposite directions is available and the anvil can operate to deform the legs of the staple after they have passed through the body tissue. In applications where access to the tissue is from only one direction, the anvil may deform the crown of the conventional staple so that its legs will project into the body tissue in a fashion so as to hold the staple against the tissue.

U.S. Pat. No. 6,884,248 Bolduc, et al., represents a class of spring like coil devices typically helical in design which can be driven rotationally in a corkscrew like manner to thread the fastener article into the tissue. This patent further describes both single and double embodiments of this device design such as coil-like devices which can be screwed into tissue to fasten it. In order to close tissue tightly, the fastener typically must have a portion of the coil configured to provide a gathering and tightening of the tissue as it is driven. Thus by design, to accomplish the goal of locking tissue the embodiment is typically configured as a spiral helical shape where the pitch and diameter are continuously shrinking. Furthermore, for the helical spiral design to be driven requires a tab or locking member to engage the driving shaft. Such features typically occlude the central portion of the fastener given the need for a large to small diameter taper of the fastener, thereby making the passage of surgical implements through the delivery system very difficult.

When the goal of the surgeon is securing or locking tissue to generate an annular port-like geometry, or a passageway, then, like the staple and classic suturing methods known in the art, the helical fastener will also require multiple deployments spaced in a circular pattern about the area to be secured. All such multiple deployment methods are time consuming and difficult to execute via typical ported access multifunctional surgical procedures.

A newer technology for fastening tissue is described in a series of patents to Carley and coworkers, for example U.S. Pat. No. 7,001,398 Carley et al., and U.S. Pat. No. 6,623,510 Carley et al. These novel fasteners represent a class of annular serpentine looped spring like devices which are essentially planar at rest and annular in a defined "transverse configuration" which is used for the delivery of the device to the surgical site.

These embodiments are comprised of a uniform geometrical backbone portion having a continuous serpentine path of looped elements which are generally symmetrical in construct and geometrical relation. Barbs are attached to some of these serpentine elements, and project inward in the relaxed planar state. They are activated by insertion of a central stabilizing core, forcing the devices from a planar arrangement to an annular configuration. The annular configuration is unstable without the central core. Upon removal of the central stabilizing core, the device folds back to the original configuration, gathering tissue that lies under its pointed projections.

A drawback of these devices is that the symmetrical composition of serpentine features and their location are only stable while a solid core is inserted through the center of the planar object to make the transverse form. If the devices are inserted on the inside of a tube in the transverse configuration, the tips of the barbs will rotate inwards to meet in the center of the tube, or to meet the tube walls, thus obstructing the tube and perhaps preventing proper delivery. The requirement for maintenance of a central internal core element within the delivery system to hold and maintain the embodiment in the transverse position, to stabilize and manage the device overall annular size and annular condition, prevents the passage of other instruments through the central core of the tissue fastening device while a fastener is in place for delivery. Thus, it is very difficult with the Carley device to deliver a tissue fastener, whether from the outside of a stabilizing core or of a tube, and simultaneously observe its placement with an endoscope or similar device. It is also very complex, if at all possible, to provide a tissue closing device near the site of operation while conducting other procedures. Instead, the endoscopic instrument must be removed, and a tissue fastening device then inserted.

The improved device of the present invention provides a self closing tissue fastener, and a delivery system therefore, that overcomes these deficiencies of the current art. The device and system provide both a clear space in an endoscopic surgical device for access to the surgical site through which instruments may easily pass, and means for storing and delivering one or more self-closing tissue fasteners close to the operative site and inside the endoscope-passing instrument, thereby creating a unique, more easily managed overall approach to tissue management, tissue visualization and closure. A key difference between the devices of the invention, and the devices of Carley et al., is that the inventive devices have a stable ring (rather than an unnecessarily flexible folded serpentine wire), to which tissue-affixing elements and novel stabilizing elements are affixed. This geometry prevents the points of the tissue fastener from moving inward, even when stored inside of a hollow tube, until the fastener is delivered to tissue. In addition, the ring serves as a torsional energy storage device, and there may be discrete zones in the ring where torsional energy is localized, interspaced with robust stiffening axial zones. These features also serve to stabilize the fastener in storage near the site of use. As a final benefit, the improved fastener of the invention can be moved from its planar state to an activated transverse state by finger pressure. The fastener can thus be loaded rapidly into a delivery device during an operation, if required or convenient.

SUMMARY OF THE INVENTION

It is an object of this invention to provide a self closing fastener which can secure or close an incision or wound.

It is an object of this invention to provide a self closing tissue fastener which will overcome the need for multiple staples, helical fasteners or suture-style array-like geometrical patterns to generate an annular port geometry in single or multilayer tissue.

It is an object of this invention to provide a self closing tissue fastener which can be secured to tissue with the expressed purpose of anchoring or securing other devices, fasteners and the like.

It is an object of this invention to provide a self closing tissue fastener with a geometrical relationship of embodiments such that when the fastener is placed within the delivery system, a significant annular non obstructed space, optionally and preferably central within the delivery system, is possible.

It is an object of this invention to provide a self closing fastener and fastener delivery and deployment system which provides a clear, unobstructed, channel to the surgeon through which other surgical instruments, apparatus, diagnostic devices, or control, closure or manipulation devices for tissues may be delivered to the surgical site, while retaining the ability to deliver one or more tissue fasteners to the site as needed. The channel is preferably sealed or sealable sufficiently to allow the use of vacuum through the channel for the manipulation of tissue.

It is an object of this invention to provide a self closing tissue fastener which has a geometrical relationship of components such that when the fastener is placed within the delivery system, with an unobstructed, optionally sealed, channel, there can exist potential energy in integrated torsion geometry domains of the fastener embodiment which, upon release from the delivery system, will, without additional assistance from deploying instrumentation, provide energy to drive tissue piercing fasteners to pierce, securely engage, attach to and remain secure within the tissue, thus self locking the device in place while locking the engaged tissue into a preferred condition as the self closing fasteners change from the deployed condition to the closed, tissue-locking condition.

It is an object of this invention to provide a self closing tissue fastener within a delivery system having an open channel, which can manipulate and shape tissue within or into the unobstructed central channel for the manipulation, control of or securing of said tissue, and/or establishing and maintaining a connection and/or contact position within the body to said tissue so that other surgical instruments, apparatus, diagnostic, tissue control, closure or manipulation devices may be delivered or passed through said secured tissue via said channel, and whereby said tissue fastener will remain secured until released. All such tissue manipulation as described is unobstructed and unimpeded by the stored fastener located within the delivery system

DESCRIPTION OF THE INVENTION

Figure 1:
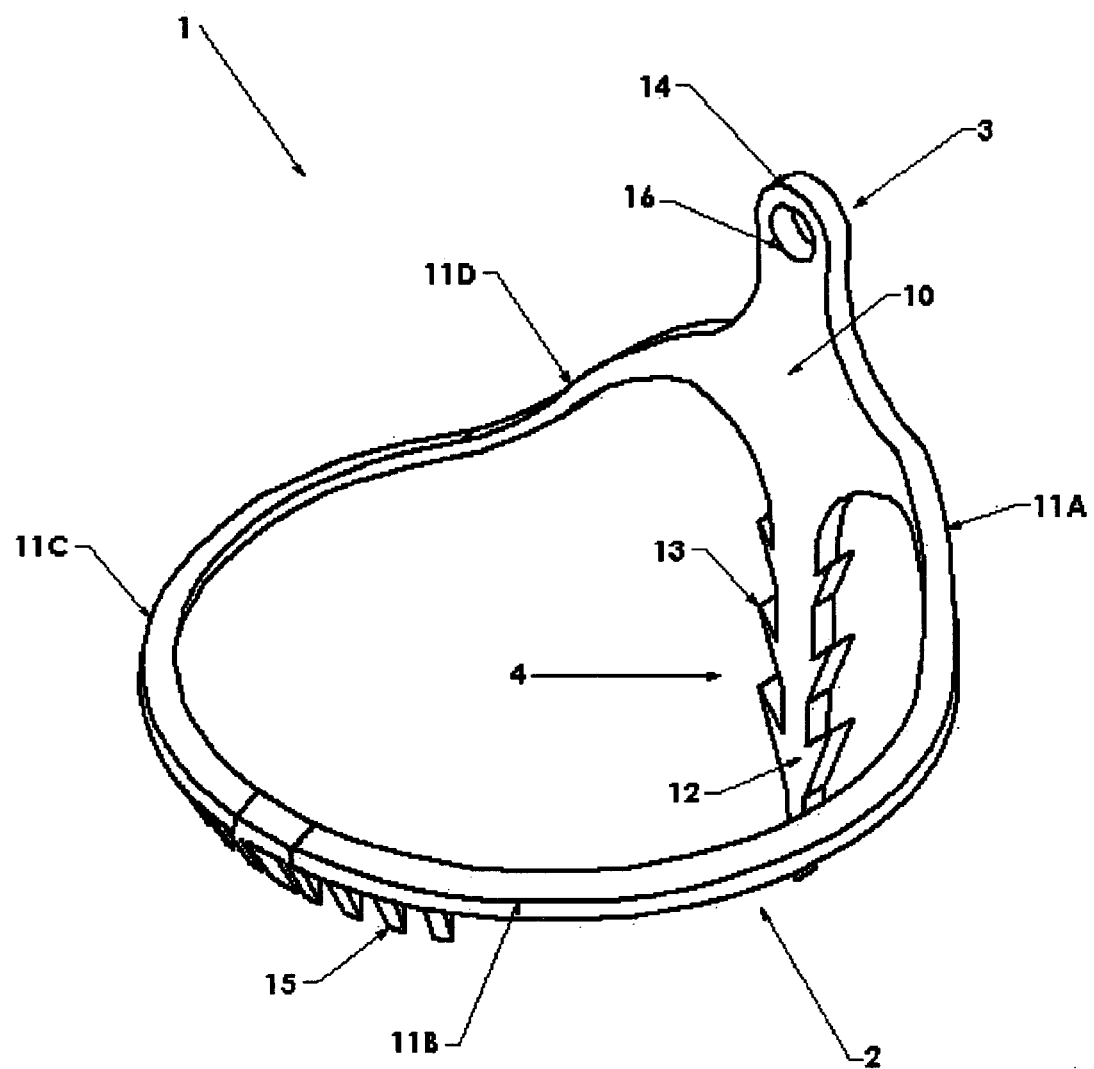
FIGS. 1 and 2 show a first embodiment of the tissue fastener of the invention, having only one tissue-affixing projection.

The fastener in the preferred embodiment of the present invention comprises an annular hoop or ring-like portion (a "ring" in the following discussion). The ring has one or more integrated tissue piercing members (also called elements) projecting from the ring on one side (edge), and one or more stabilizing members projecting from the ring on the other side. In a preferred embodiment of the present invention, each of the one or more zones carrying piercing or stabilizing members are integrally interconnected to an adjacent second zone. The second zone is specifically designed and configured to provide a torsional or rotational energy storage component to the tissue piercing and/or tissue surface interacting zones.

Energy is stored in the ring when the ring is deformed from a first, essentially planar configuration to a second annular configuration, the annular configuration having an open annular space within the ring, of substantially the same diameter as the ring. This stored torsion rotational energy enables the tissue piercing and stabilizing zones to translate from an open, annular, virtually cylindrical stored condition with high, releasable potential energy, to a closed, "deployed", relatively planar orientation upon completion of a deployment process. Release of the fastener from the device allows the release of the stored potential energy of the fastener to close openings in tissue.

The released energy is stored in the torsion zones of the fastener when the fastener is loaded into the deployment mechanism. The loading action rotates the tissue interacting members in relation to the torsion members when the tissue-interacting members are deformed from a relatively planar geometry to a relatively cylindrical or annular geometry.

The resulting annular geometric condition of the fastener, when placed within a deployment apparatus, provides a significant advantage to the physician, by providing a clear, unobstructed, optionally sealed, space within the apparatus through which other instruments or diagnostic devices may pass, without interference between the other instrument and the annular configuration of the fastener. This allows one or more fasteners to be deployed close to their site of use at the beginning of a procedure; they can be used to close the site without having to remove the endoscope and replace it with a fastener delivery device.

In describing the functionality of the preferred embodiments in this application, geometrical terms such as "hoop", "ring", "annular", "cylindrical", "volumetric", "channel" and "planar" have been used to illustrate to the reader the spatial inter-working relationships and attributes of the key elements, sub elements, tissue structures and interactions between and among entities. One skilled in the art can further appreciate that the use of these specific terms are not intended to restrict or limit the scope of the preferred embodiments describe herein from being further comprised wholly or any portion thereof of additional or unique geometric, spatial or interacting physical geometrical entities.

For example, the generally cylindrical geometric condition and associated volume of the basic preferred embodiment, in its higher energy annular form, is advantageous due to its minimal perimeter and maximum volume. However, the preferred embodiment may also adopt any number of closed perimeter profiles which generate volume such as "square" "rectangular" "triangular" and the like and/or smooth closed perimeter profile curved forms such as elliptical or oval and similar forms, and any generally convex combinations thereof.

Such geometrical entities, definitions, constructs features and/or construction controlling entities and the like may be defined and/or described as but not limited to; "triangles", "polygons", "squares", "rectangles", "splines", "arcs", "circles", "curves", "spheres", "projected features", "deformed features", "projected surfaces", "deformed surfaces", "lofted features" and/or "lofted surfaces" and includes any portion wholly or in part and/or sub portion thereof which may be used to define a preferred embodiment configuration or a portion thereof and in doing so, provide a unique and/or more improved functionality to the basic preferred embodiment.

Figure 2:
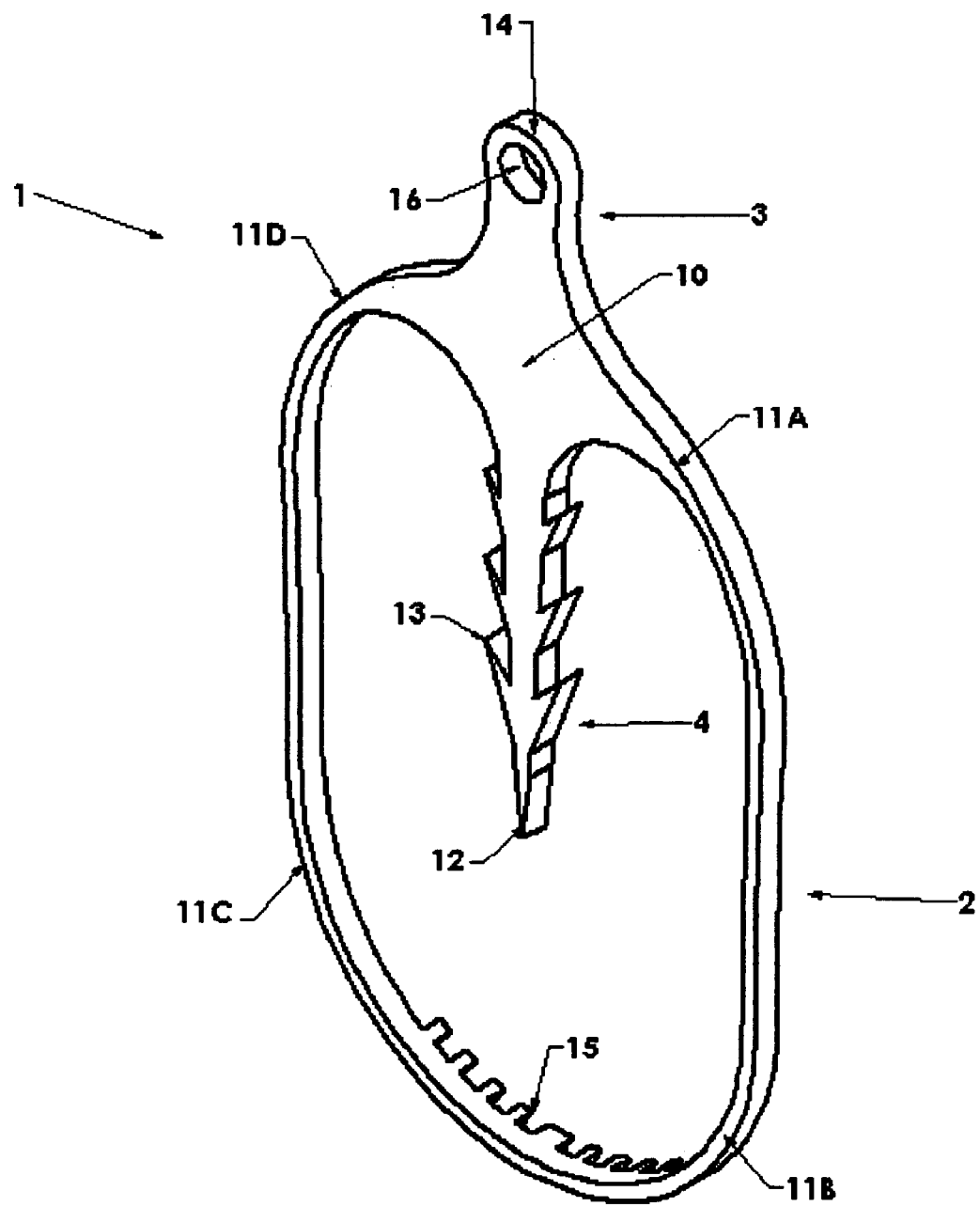

FIG. 1 and FIG. 2 show perspective views of an embodiment of the present invention, namely a self closing tissue fastener device in its most basic functional embodiment. FIG. 1 and FIG. 2 detail the fastener function and key system geometrical entities that comprise a preferred embodiment of the present invention. It can be defined in its simplest construct in FIG. 2 which shows the self closing fastener in the tissue locking condition. This is also typically a planar configuration, and typically the device is manufactured so as to be originally in this state.

The device 1 has a generally ring-like configuration, comprising a ring 2 and at least one pair of projecting members 3, 4 extending from each side of the ring. The ring 2 has several functional zones, which in this embodiment comprise zones 10, 11A, 11B, 11C and 11D. Zones 11A and 11D are twistable zones, which can absorb at least a 90 degree twist during activation, and which will also recover more than about 50% of said twist when released. Zones 11B and 11C, connecting zones 11A and 11D, may be relatively resistant to deformation under torque, or may have similar underlying mechanical properties to the materials in zones 11A and 11D. For simplicity of manufacture, it is preferred to make the device 1 from a single sheet of material, by cutting, etching, stamping, or other conventional mechanical fabrication method. Cutting by etching with acid is a preferred method.

The projecting members 3, 4 comprise a central zone 10, which comprises an integrated tissue piercing member 12. Piercing member 12 may preferably contain one or more securing tissue interacting members 13 ("barbs"), which as illustrated project toward the center of the device in its planar form (FIG. 2). Optional tissue gripping teeth 15 reside on and are preferably integral to the ring 2 as a linker between zones 11B and 11C. Central zone 10 also will normally include a stabilizing member 14. Stabilizer 14 may also include annular or locking embodiment features, such as hole 16 for example, to secure or attach other devices, sutures, stapes or connecting entities.

In the embodiment shown in FIG. 1 and FIG. 2, the length of tissue piercing member 12 reaches to about the center of the ring 2 in the planar state (FIG. 2). The overall length of zone 10 and its associated projections 3 and 4 may alternatively be constructed to be sufficiently long to span the relatively annular opening defined by ring 2 including its zones 11A, 11B, 11C and 11D respectively, with the embodiment in the planar condition of FIG. 2 (not illustrated). Such an embodiment would allow members 12 and/or 13 to interact directly with feature 15 in a predefined manner, and/or compress tissue that is trapped in or about zone 10 and tissue-piercing member 12, and features such as teeth 15, thereby locking the tissue so that it cannot readily escape from the fastener.

Torsion rotational energy is imparted to the preferred embodiment as it is physically driven in shape from the planar orientation of FIG. 2 to the cylindrical orientation of FIG. 1, and then placed in a delivery mechanism which secures it in its high energy open state. In a simple method, as described in this embodiment, the planar form of device 1 as shown in FIG. 2 is converted to the stressed form of FIG. 1 by being passed over a solid mandrel, typically round or having a reasonably smooth contour. The stressed form can then be stored on either the outside or the inside of a tube or other hollow object, which provides a constraint preventing the device 1 from rotating from the general shape shown in FIG. 1 back to the lower-energy planar state as shown in FIG. 2. The stressed form will revert to its original state only when released from the constraint. In contrast, the most similar prior art device cannot be maintained in a stable state in the interior of a tube, as will be explained below.

Torsional energy is imparted to the device 1 during the rotation of central spine zone 10 and its projections 3, 4 with respect to the other zones of ring 2, to obtain an annular orientation of the device. The annular form is then stored in a placement device. Upon release from the placement device, the spring-like zones 11A and 11D, along with energy stored within the overall spring-like ring 2, drive the central spine zone 10 and its tissue interacting geometry members rotationally from a condition like that shown FIG. 1, to a condition like that shown in FIG. 2. If the tip of tissue piercing member 12 has been inserted into tissue, the tissue will be locked by the device after the device has returned to an approximately planar orientation.

It should be noted that to achieve this effect, the band 2 must be relatively resistant to stretching in diameter, since if it stretches easily; the fastener may be able to escape from the carrier under some conditions. One criterion for the material of the band is that it cannot be stretched by more than about 50% in circumference without failure, thereby providing dimensional stability to the tissue closure. The circumference for this purpose is the path length of the outside edge of the band when it is in the configuration shown in FIG. 1.

While this embodiment clearly demonstrated the basic functional and ancillary feature aspects of the torsion energy driven rotational closing system of an embodiment of the present invention, it is not capable of demonstrating the utility and enhanced security of a multiple point engaging self closing tissue closing device embodiment. These enhanced superior functional preferred embodiments which also provide for a clear unobstructed sealed, centrally located, volumetric space within the delivery system will now be defined and described within the figures and descriptions that follow.

Figure 3:
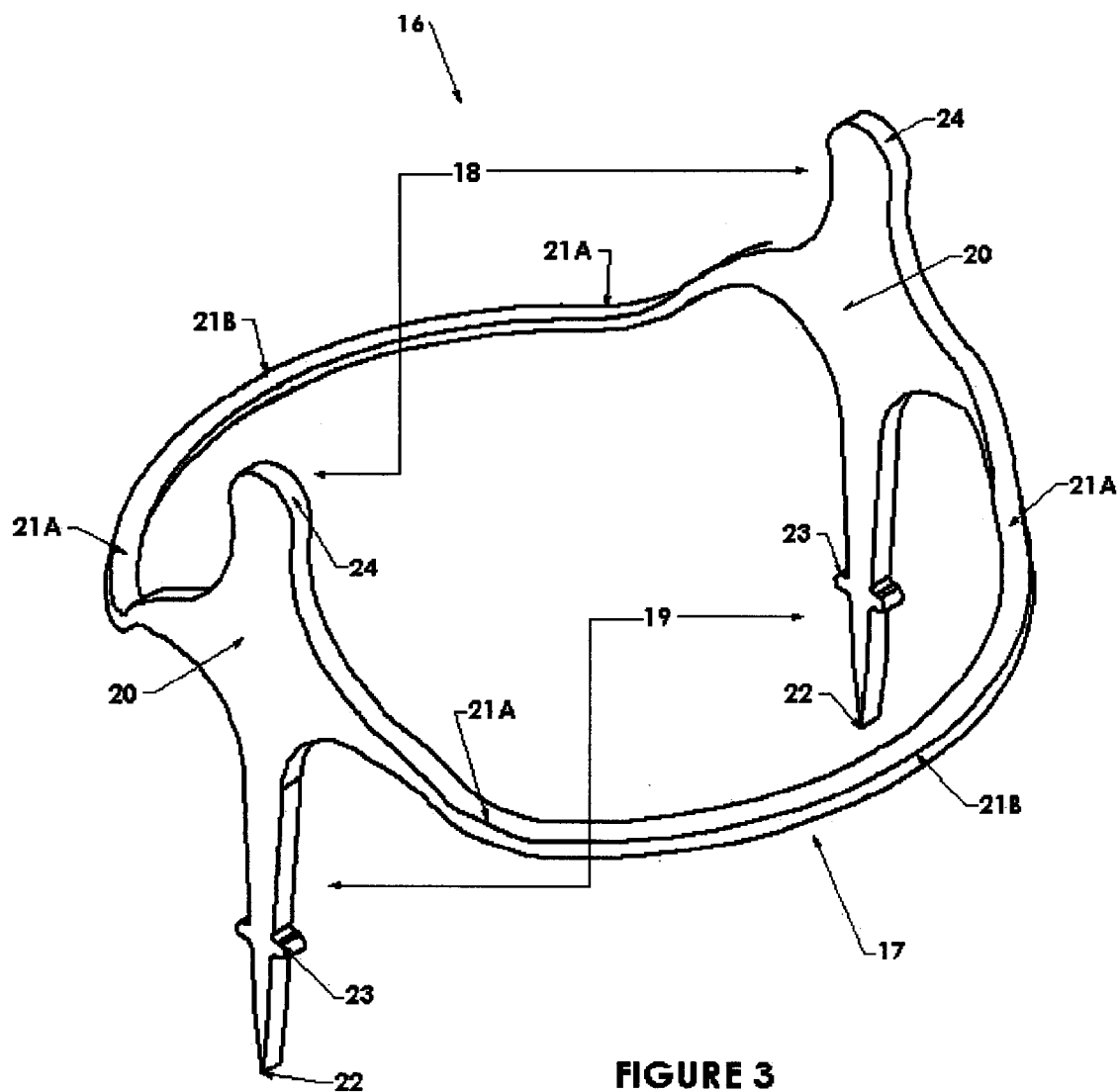
FIGS. 3 and 4 illustrate a second embodiment of the fastener.
Figure 4:
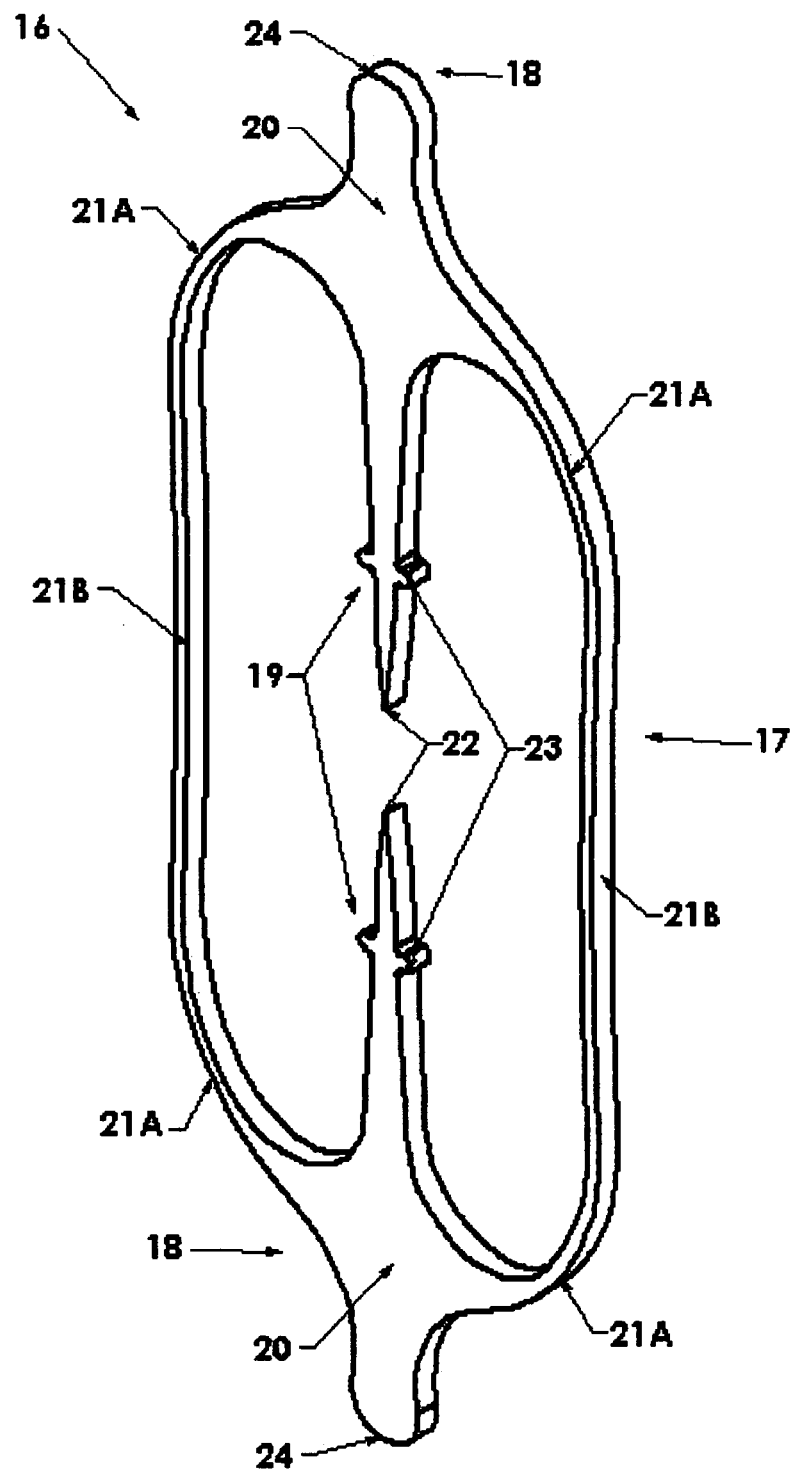

FIG. 3 and FIG. 4 show perspective views of a preferred embodiment of the present invention demonstrating a multi element tissue engaging configuration of the self closing tissue fastener device. The device 16 in this embodiment has a generally ring-like configuration, comprising a ring 17 and multiple projection members 18, 19 extending from each side of the ring. In this embodiment the projection members from the ring 17, shown as features 18 and 19, are symmetrical in spacing. The ring 17 has several functional zones, which in this embodiment comprise multiple independent zones along the ring annulus 20, 21A, and 21B respectively. Zones 21A are twistable zones, which can absorb a 90 degree twist during activation, and which will also recover at least about 50% of said bend when released. Zones 20 and connecting zone projection member features 22, 23 and 24, may be relatively resistant to deformation under torque, or may have similar underlying mechanical properties to the materials in zones 21A and 21B. Zones 21B may be like either zones 21A or zones 20 in torque properties, or may be intermediate. In a preferred embodiment, the entire device is made from a single sheet of material.

Zones 21A, are connected to the geometric interconnecting zone 21B and central tissue engaging zones 20 in a smooth integrated blended manner, thus forming in their entirety the closed generally annular ring like space defined by ring 17, surrounding a central area, with multiple projections 18, 19 projecting from zones 20. Preferably, the integration is achieved by making the entire fastener from a sheet of metal.

The multiple zones 20 comprise integrated tissue piercing members 22 and stabilizing members 24. Piercing members 22 ("spines") may preferably contain one or more securing tissue interacting member features 23 ("barbs"), which as illustrated project toward the center of the device in its planar form (FIG. 4) from ring 17. Stabilizers 24 project outwardly. In an alternative embodiment, not illustrated, the barbs 23 could point outwards and the stabilizers 42 could point inwards. This would create a fastener with a significant open central space in the closed, tissue-locking configuration.

The planar form of this embodiment device 16 as shown in FIG. 4 is converted to the stressed form of FIG. 3 by being passed over a solid mandrel, typically round or having a reasonably smooth contour. Alternatively this multiple zone embodiment 16 may be squeezed diametrically, for example manually, such that member 20 and associated features rotate to an axial alignment condition. This stressed embodiment can then be inserted into a hollow cavity such as a tube which will constrain and maintain the embodiment in the axial stressed form. The stressed form attained through either configuration method can then be transferred and stored on either the outside or the inside of a tube or other geometrically hollow object, which provides a constraint preventing the device 16 from rotating from the annular shape shown in FIG. 3 back to the lower-energy planar state as shown in FIG. 4. The stressed form of the embodiment will revert to its original state only when released from said constraint geometry.

In the embodiment show in FIG. 3 and FIG. 4, tissue interacting member 22 is shown as a piercing geometry construct and member 23 may be viewed as a tissue stopping construct which further imparts a compression locking force to the tissue pierced by feature 22.

In describing a preferred embodiment of the present invention, one skilled in the art can fully appreciate and understand that many tissue interacting features for securing and management have been described such as those found for example within U.S. Pat. No. 7,112,214 Peterson et al., U.S. Pat. No. 6,746,460 Gannoe et al. and U.S. Pat. No. 6,623,510 Carley et al. Therefore, any number of combinations and location of piercing, locking, grabbing, hooking, spearing clamping and/or securing type geometries, coatings and/or materials may be defined and placed along or attached anywhere in proximity to central zone 20 or on, along and/or integral to torsion members 21A and connecting members 21B to achieve a desired effect on tissue when the self closing fastener is actuated.

Such embodiment features may also be geometrically interlocking and/or non symmetrical in design location or spatial deployment. The numbers of torsion members like 21A has to be twice the number of member elements 20, as drawn, and the number of elements 20 may be an even number, as illustrated, or an odd number. Teeth analogous to those illustrated in FIG. 1 as element 15 may be present. These features and/or any portion or sub portion thereof of the functions as described by fastener members 20, 21A, 21B, 22, 23 and 24 inclusively may be dissimilar in composition, non planar in nature and/or non axial in alignment and/or non symmetrical in spacing and/or spatial position and/or location, thus providing additional options in securing tissue.

Figure 5A:
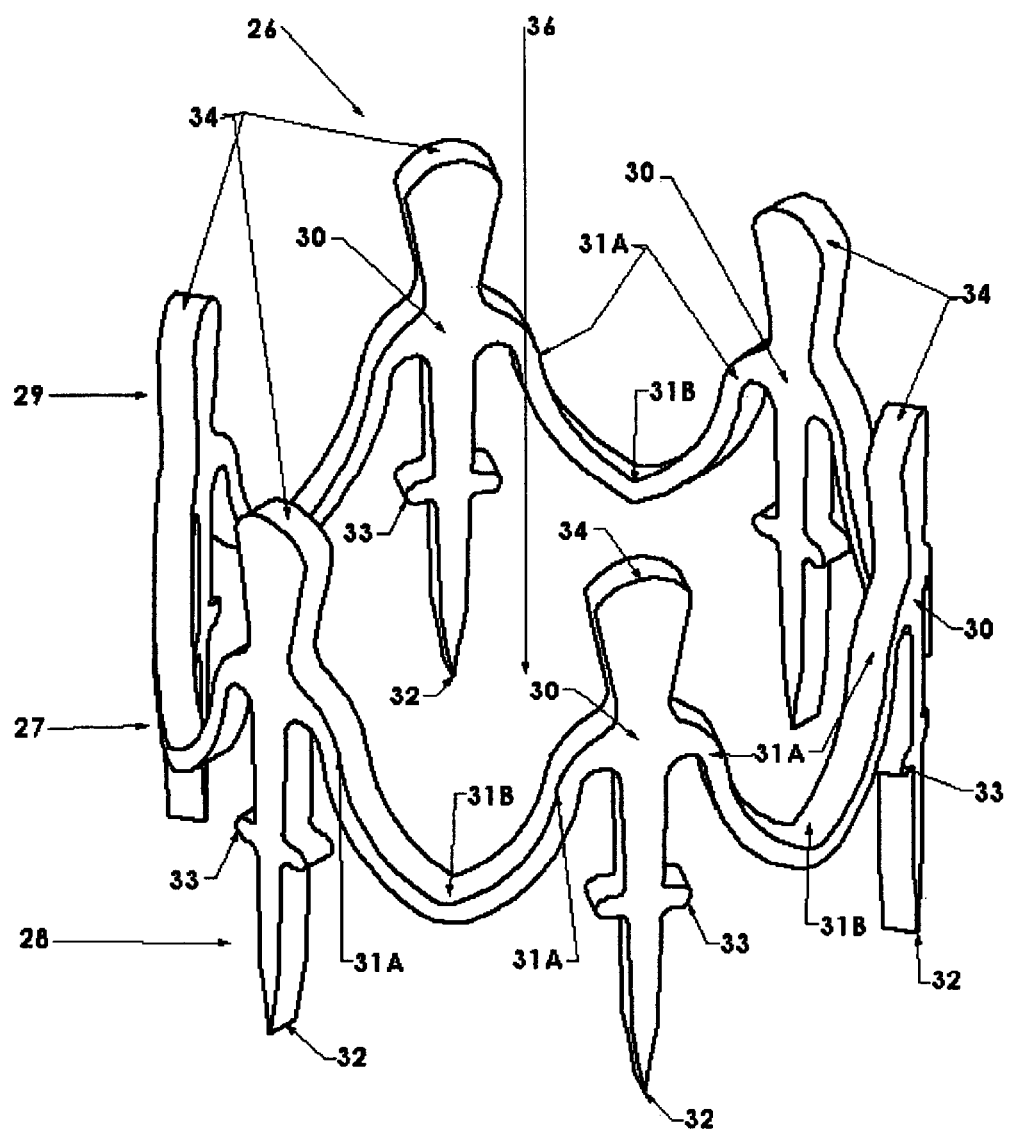
FIGS. 5A, and 6 illustrate a preferred embodiment of the fastener.
Figure 5B:
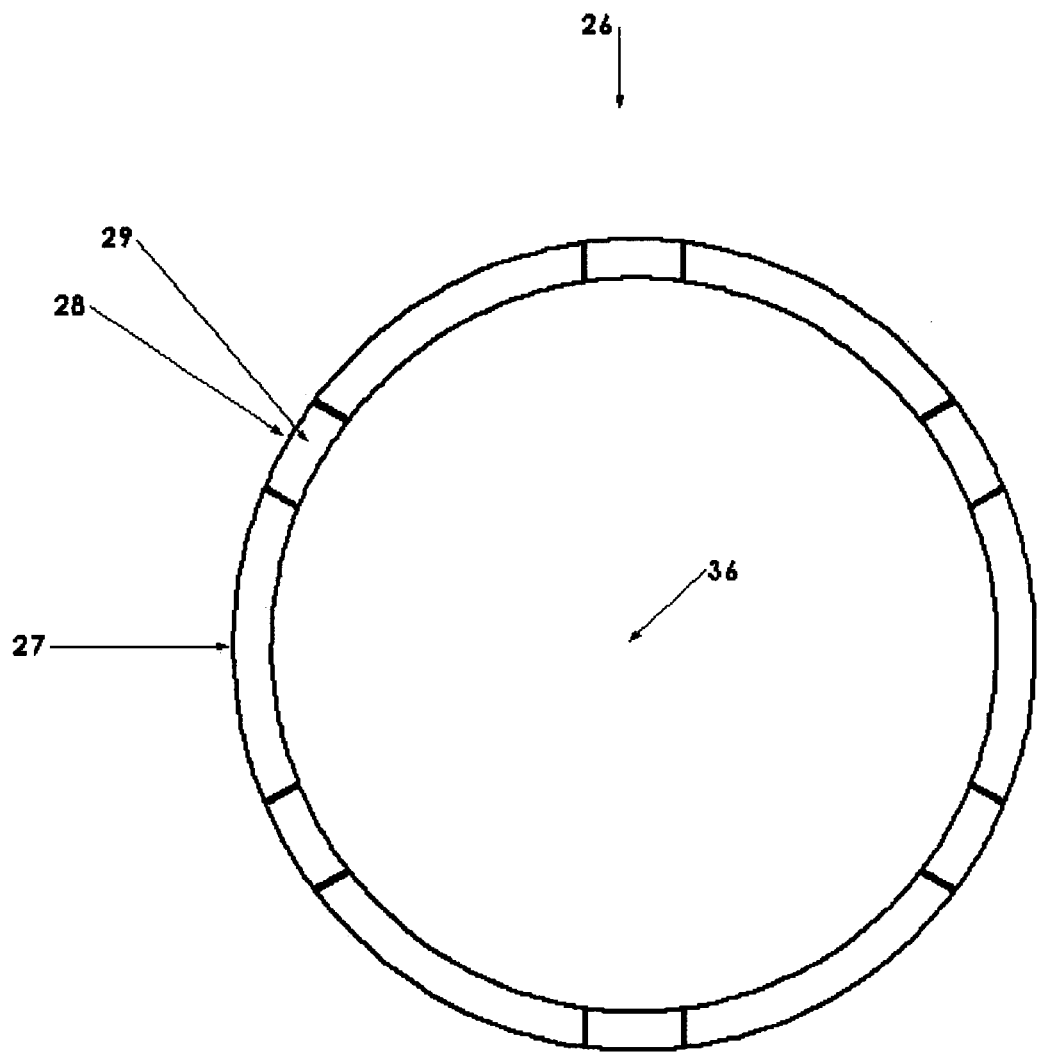
FIG. 5B is an axial view of the device of FIG. 5A.
Figure 6:
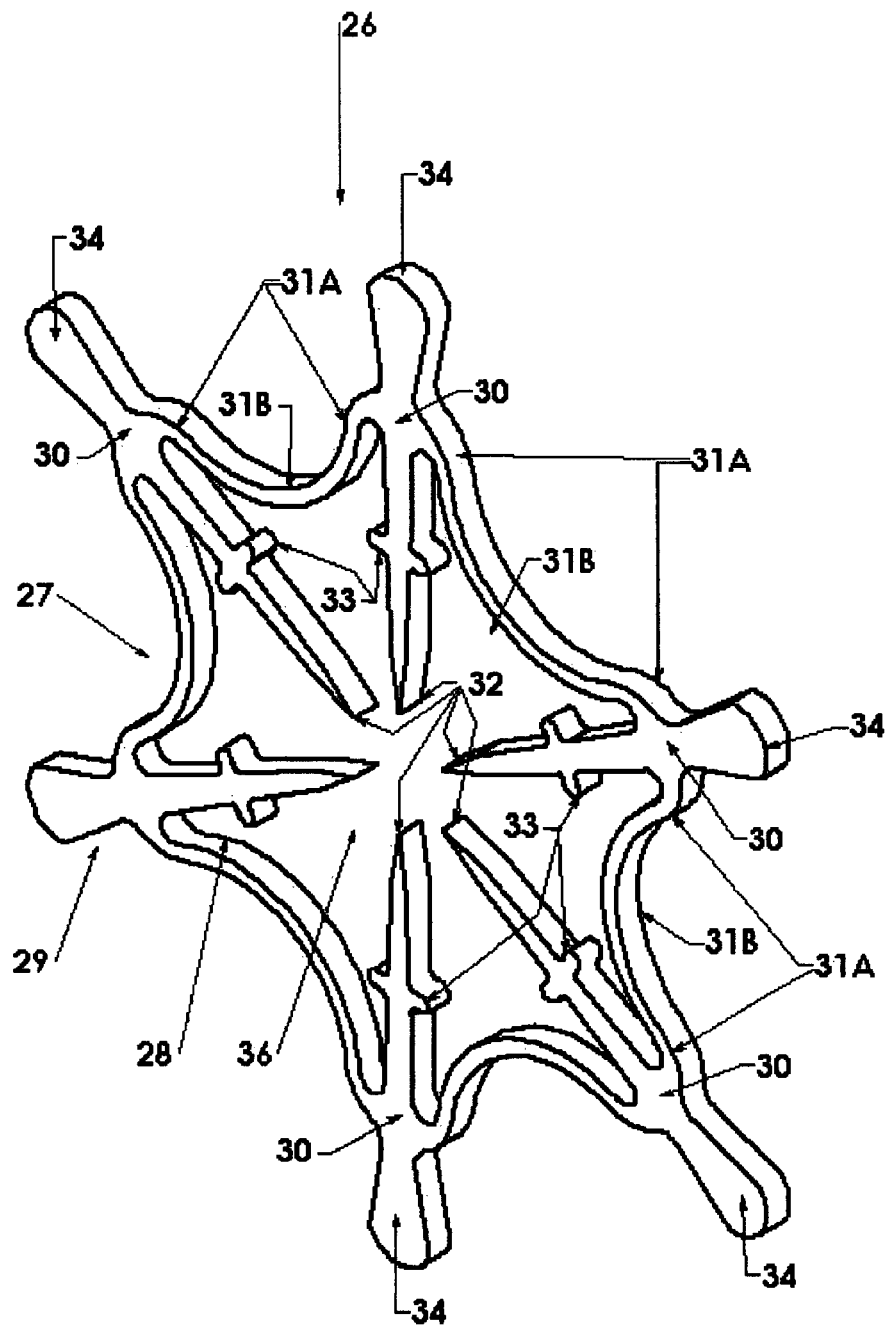

FIGS. 5A, 5B and FIG. 6 show perspective views (FIGS. 5A, 6) and an axial view (FIG. 5B) of a preferred embodiment of the present invention which demonstrates the key parameters for multi-element, multi-directional tissue engaging geometry as a self closing tissue locking fastener embodiment.

The device 26 in this preferred embodiment of the present invention has a generally ring-like configuration, comprising a ring 27 and multiple projection member features 28, 29 extending from each side of said ring. In the illustrated embodiment, the projection members from the ring 27, shown as features 28 and 29 are multiple in nature and symmetrical in spacing. The ring 27 in the annular configuration of FIG. 5A defines a central area 36 (best seen in FIG. 5B). The ring 27 has several functional zones, which in this embodiment comprise multiple independent torsional zones 30, 31A, and 31B along the ring annulus. Zones 31A are twistable zones, which can absorb at least a 90 degree twist during activation, and which will also recover at least about 50% of said bend when released. Zone 30 and connecting zone features 30, 32, 33 and 34, may be relatively resistant to deformation under torque, or may have similar underlying mechanical properties to the materials in zones 31A. Zones 31A are connected to the interconnecting zones 31B and central zones 30 in a smooth manner, thus forming in their entirety the closed generally annular ring 27 which surrounds an area 36. Connecting zones 31B may have the same mechanical properties as one the zones they connect, or be intermediate.

Ideally, recovery of the positions of the spines 32, upon return from the annular to the planar configuration, with the spines 32 embedded in the tissue, is substantially complete, i.e., nearly 100%. However, some permanent distortion may occur during the conversion of the device from the planar form to the annular form. Moreover, the tissue itself may prevent complete return of the spines 32 to the planar configuration. In many situations, a significant residual bend is acceptable, since opposed tissue-piercing members disposed around the perimeter of a ring will collectively hold the fastener in place even with a significant degrees of residual deformation. It is believed that an approximately 50% return to the original position will prove to be effective in most situations, and in some cases a higher degree of residual deformation may be acceptable, depending on the particular tissue and the type of stresses placed on the tissue.

The projection members comprise multiple central zones 30, with attached features which comprises an integrated tissue piercing member 32 and stabilizing member 34. Piercing member 32 may preferably contain one or more securing tissue interacting members 33 ("barbs"), which as illustrated project toward the center of the device from ring 27 in its planar form (FIG. 6).

Said zones 30 also may include a load stabilizing and deployment position location member 34. It may have any number of different or multifaceted tissue interacting barbs 33 arrayed along projection from the tip of piercing member 32 to the central spine connecting the junction of zone 30 and zone 31A features respectively. In addition, tissue interacting geometry may also be defined in a preferred embodiment as projecting from or integral to torsion members 31A and connecting members 31B, in like wise fashion as described for members 11A-11D and 15 in previously described FIGS. 1 and 2 respectively. In the embodiment of FIGS. 5A and 6, there are a sufficient number of zones 30 that stabilizing projections 34 need not be present on every zone 30.

The planar form of this embodiment device 26 as shown in FIG. 6 with minimal enclosed open area 36 is converted to the stressed annular form of FIG. 5A and maximum area 36 by being passed over a solid mandrel, typically round or having a reasonably smooth contour. Alternatively as in the previous example this multiple zone embodiment 26 may be squeezed diametrically, for example by squeezing the projections 34 together, so that zones 30 rotate to an axial alignment condition. FIG. 5B shows an axial view of the embodiment in this condition, and its open central space 36 is easy to visualize in this projection.

This stressed embodiment shown in an axial view in FIG. 5B generated by either method can then be inserted into a hollow cavity such as a tube which will constrain the embodiment in the axial stressed form. The stressed form can then be transferred and stored on either the outside or the inside of a tube or other geometrically hollow object, provided that the geometry selected provides a constraint preventing the device 26 from rotating from the general shape shown in FIG. 5A back to the lower-energy planar state as shown in FIG. 6. In the preferred embodiment of the present invention, it is intended that the stressed form of the fastener 26 embodiment will revert to its original state only when released from said constraint geometry.

In the preferred embodiment show in FIG. 5A and FIG. 6, tissue interacting member 32 is shown as a piercing geometry construct and member 33 may be viewed as a tissue stopping construct which further imparts a compression locking force to the tissue pierced by feature 32.

The preferred embodiment shown in FIGS. 5A 5 B and FIG. 6 provides a sizeable clear annular central region 36 for the passage of instruments when the self closing tissue fastener is residing within the placement and deployment apparatus. Furthermore this embodiment by design may be geometrically configured to engage and lock tissue yet leave a defined smaller central unobstructed zone 36 in the tissue locking position (FIG. 6) where access through the tissue that has been fastened by the self closing fastener may be created and maintained. Such devices as a stoma style port or plug for example may be secured without interference from the deployed fastener features. As noted above, a larger central zone can also be created, if needed, by having the tissue-affixing spines 32 pointing outward; or by having the spines 32 shorter in length.

FIGS. 7-10

FIGS. 7-10 show perspective and sectional views of a preferred embodiment of the present invention placed within a deployment device that enables tissue manipulation, site placement and fastener deployment of the self closing tissue fastener.

Figure 7:
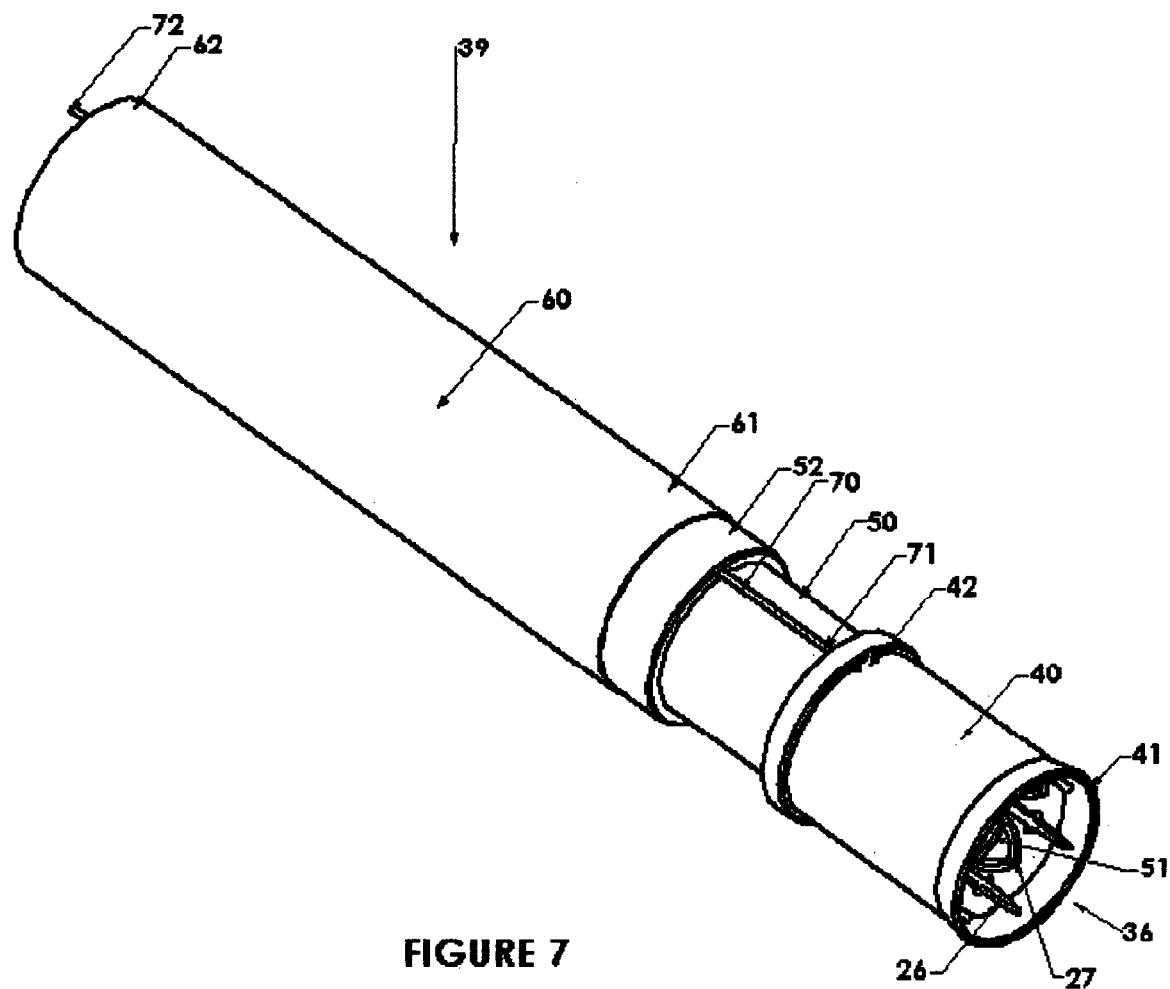
FIGS. 7 and 8 illustrate the preferred embodiment residing within a representative endoscopic instrument delivery system.
Figure 8:
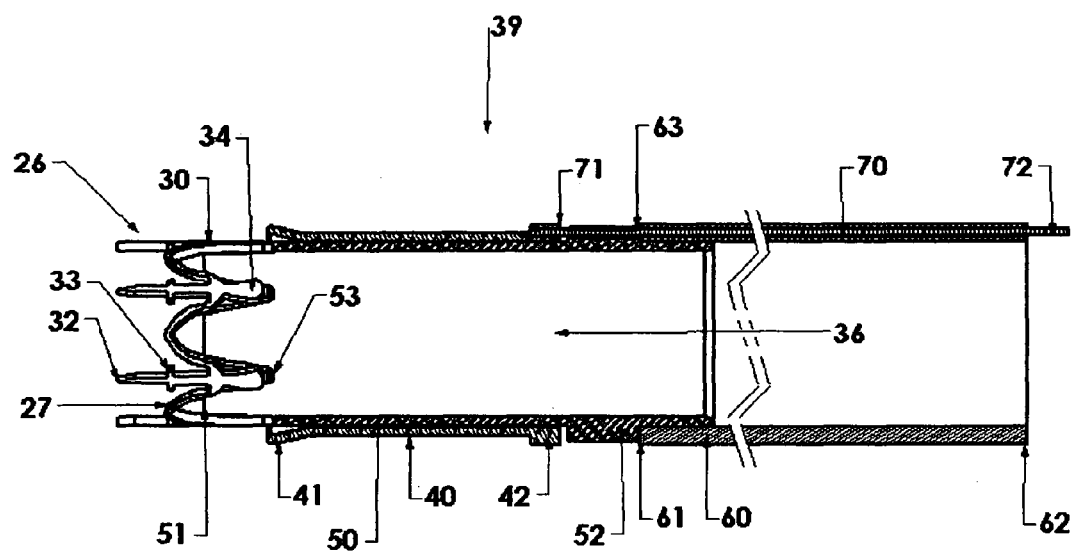

FIGS. 7 and 8 describe a preferred embodiment of the positioning and deploying apparatus which can effectively deliver and deploy the self closing tissue fastener to the surgical site while maintaining a significant unobstructed central volume in the instrument for surgical and endoscopic instruments to pass. FIG. 7 is a perspective views of the delivery system 39 with a fastener 26 (i.e., a fastener of the embodiment shown in FIGS. 5 and 6) in the stressed annular condition, before deployment of the fastener begins.

FIG. 8, a cross sectional view, shows the delivery system 39 in a fastener deployment condition where the fastener 26 in the stressed configuration shown in FIG. 5 is shown residing within and just held by an outer tubular like retaining member 40 with a proximal end 42 and distal end 41. A clear unobstructed area 36 is defined by this apparatus configuration through which other surgical instruments, apparatus, diagnostic or tissue control, closure or manipulation devices may pass.

Referring to FIG. 7, a preferred embodiment of fastener 26 is residing within and against the inner wall of tubular outer shell like member 40. Shell 40 comprises a distal tissue contact end 41 and a proximal actuating end 42. It is an advantage that fastener 26 is covered by tubular outer shell 40 such that the tissue engaging features 32 of fastener 26 are not exposed and so cannot inadvertently engage tissue during manipulation of the instrument. Shell 40 is located at the distal end of tubular member 50 with fastener 26 residing within. The delivery apparatus 39 holds the fastener 26 in the stressed state in this configuration, and with fastener 26 held in position, delivery apparatus 39 is easily manipulated within the surgical site.

Shell 40, tubular member 50 and endoscopic delivery tube 60 are preferably all sealably connected. which also provides a significant advantage to the surgeon in that a sterile field can be maintained within the central area 36 of the instrument and a vacuum force can be transmitted to the distal end of the apparatus 39.

Referring to FIG. 8, showing the relationship of key features, proximal end 42 of member 40 is attached to a deployment pull wire member 72 at the distal end 71 of wire 70. Pull wire member 70 resides within a secondary lumen 63 of endoscopic instrument delivery tube 60. Delivery tube 60 is connected at the distal end 61 to a second axial tubular member 50 at proximal end 52. Distal end 51 of tubular member 50 resides, preferably sealably, within outer tubular shell member 40. The distal end 51 of tube 50 is essentially identical in diameter to the diameter of fastener 26 when fastener 26 is in the stressed or annular state, as illustrated in FIG. 8.

Shell 40 is axially slidable along the outer surface of tubular member 50 from distal end 51 toward proximal end 52 respectively. In the preferred embodiment, shell 40 is in sealing engagement with tube 50 to seal their mutual contact for use with vacuum. Comparing FIG. 7 to FIG. 8, one skilled in the art can clearly understand that pull wire 70, when pulled at proximal end 72 in the axial proximal direction, will then move the shell 40 of the apparatus to deploy fastener 26. Fastener 26 is held within and released from delivery system 39 by holding relative position and then applying a relative motion between endoscopic instrument delivery tube 60 and pull wire 70.

Applying said motion on pull wire 70 will then forcibly slide member 40 relative to inner tubular member 50. Meanwhile, fastener 26, which is oriented and held longitudinally by features 51 and 53 engaging fastener guide feature 34, is pushed into the tissue located distally to tissue-piercing members 32, via force delivered via tube 60, as features 42 and 52 are brought together, thus driving and exposing fastener 26 to the release position, as shown in FIG. 8.

Endoscopic instrument delivery tube 60 and pull wire 70 are shown in a truncated length state for illustration purposes, and are not intended to be limited in length or construct. Delivery tube 60 may be comprised of flexible materials for control and direction. Numerous schemes features and constructs well known in the art may be applied at proximal end 62 of the endoscopic instrument delivery tube 60 to generate a required relative motion between endoscopic instrument delivery tube 60 and wire 70.

After fastener 26 is freed from its secure position by the release of stabilizers 34, fastener 26 rotates from the general shape shown in FIG. 5A back to the lower-energy planar state as shown in FIG. 6. Since the points of the spines 32 were forced into tissue before the fastener 26 was released, then the rotation from the annular state of FIG. 6 to the planar state of FIG. 5 drives the points of the fasteners into the tissue and towards the center of the circular area 36 (see FIG. 5B), thereby locking the tissue in position as the self-closing fastener 26 closes itself.

FIGS. 7 and 8 illustrate preferred embodiments of the positioning and deploying apparatus which can effectively deliver and deploy the self closing tissue fastener 26 to the surgical site. Preferred embodiment features of the present invention so described also can be used to manipulate and manage tissue during a surgical procedure or set and maintain an entry site portal to allow further access to deeper tissue or body organs. In the preferred embodiments described in the present invention, a sealed channel volume 35 is described as passing wholly through the center core of the fastener and the delivery apparatus and thus the whole apparatus including fastener 26 is available for the surgeon to utilize as a "virtual port".

While the preferred embodiment clearly illustrates an advantageous preferred method for safely delivering the fastener to a surgical site, one skilled in the art can clearly understand that there are a number of various combinations of annular type elements in a number of spatial arrangements and control schemes maybe conceived and assembled as a delivery apparatus to effectively secure and maintain fastener 26 in its stressed condition, as has been clearly illustrated in the previous figures, while still providing an unobstructed pathway for endoscopic instruments and the like to pass through.

Figure 9:
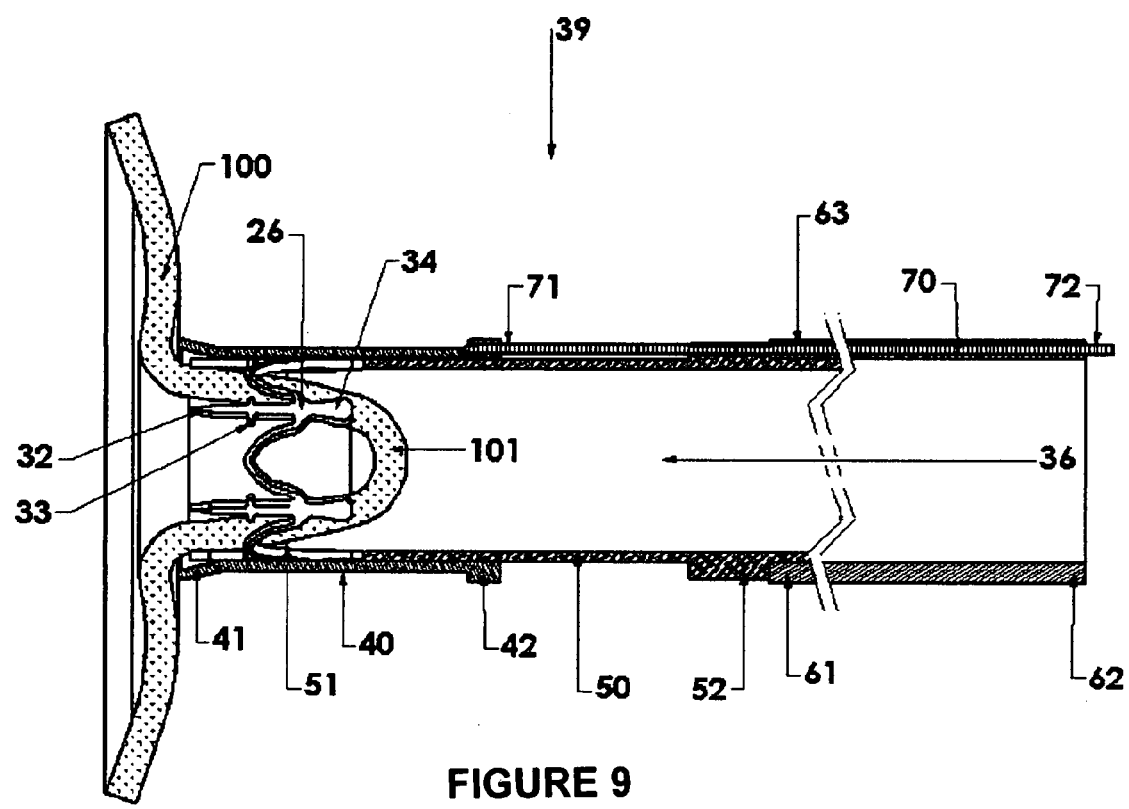
FIGS. 9 and 10 illustrate a preferred embodiment in which vacuum is used to immobilize tissue for fixation with the fastener of the invention.
Figure 10:
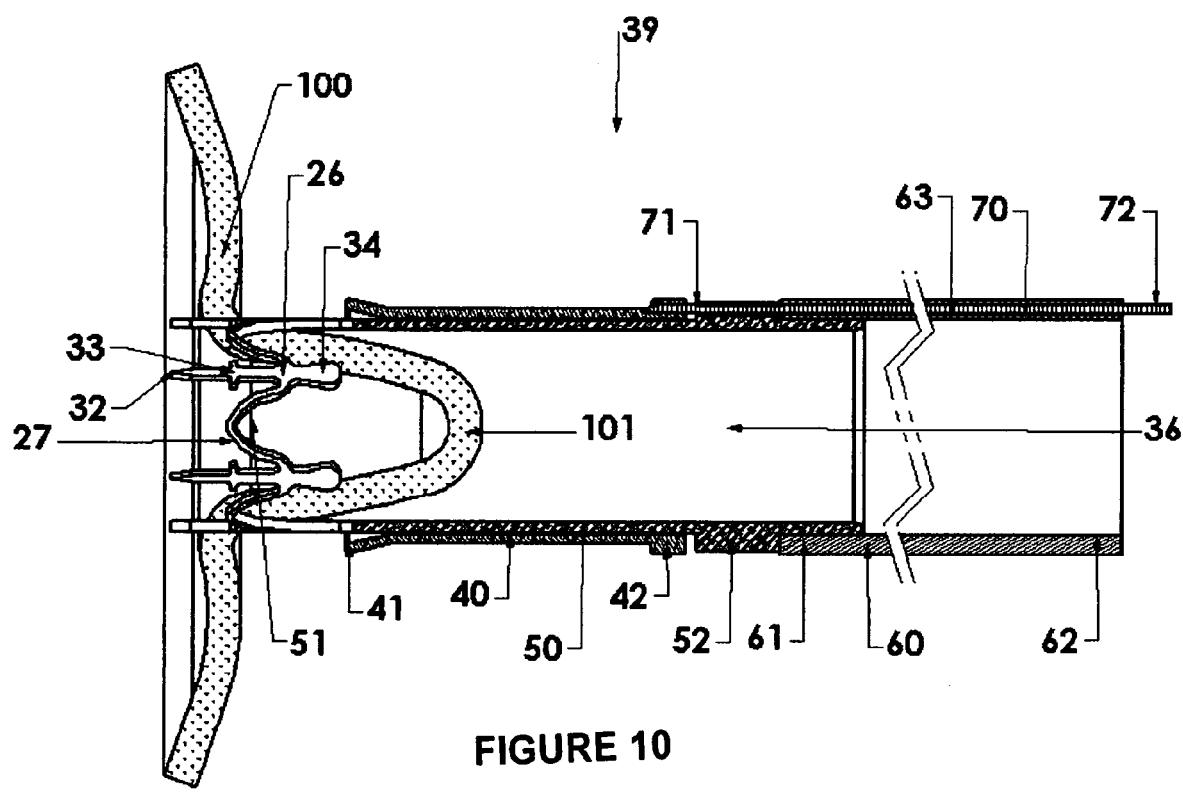

FIG. 9 and FIG. 10 illustrate in cross sectional views a method of operation which facilitates the manipulation of tissue and the location and placement of the self closing tissue fastener on said tissue. The delivery apparatus 39 shown in FIGS. 9 and 10 is functionally the same as the apparatus described in FIGS. 7 and 8 and identical numbers are used for identical parts. FIG. 9 shows a cross sectional view of the preferred fastener 26 residing within the delivery system described in FIGS. 7 and 8. The distal end of delivery apparatus 39 (feature 41) is moved within the surgical field and placed in proximity to target tissue 100. In FIG. 9, the delivery apparatus 39, consisting of elements 40, 50, 60 and self closing fastener 26 within central volume 36, with features and embodiments illustrated in FIGS. 7 and 8, is deployed to target tissue element 100.

The proximal end of the unobstructed, sealed, and preferably centrally located channel 36 is connected in a sealed manner to a vacuum source at the proximal end (not shown), and the distal end is then advanced and placed against target tissue. Energizing a vacuum source connected to tube 60 at the proximal end of the delivery apparatus 39 allows the vacuum in the tubes 40, 50 and 60 to pull on target tissue 100, thereby creating a central dome-like distended tissue mass 101 pulled in by said vacuum. The tissue 101 now resides the lumens of tubular elements 40 and 50, which are designed to be sufficiently self-sealing to maintain said vacuum force.

While the distended tissue 101 is held by vacuum force within tube 50, the self closing tissue fastener 26 is then advanced into surrounding tissue 100 as described in the discussion of FIGS. 7 and 8, thereby engaging tissue 100 with the multiple tissue piercing and retaining elements 32 and 33 of self closing tissue fastener 26.

In FIG. 10, the shell 40 is shown as being retracted, via pull wire 70, with respect to the device support tube 50, and the self closing tissue fastener 26 is now released from its confinement. It will now be able to self actuate to attain the planar condition as detailed in the description of FIG. 6. In particular, the stabilizer members 34 of fastener 26 can now rotate outwards, allowing the tissue-piercing features 32 and tissue stop features 33 to enter tissue mass 100 and affix the parts of tissue 100 together.

The tissue is then removed from tube 50 of delivery apparatus 39 by releasing the vacuum. The delivery apparatus 39 now can be withdrawn. Fastener 26 is now fully engaged with tissue 100, and remains within and locks and secures said tissue.

Alternatively, a separate catheter-like device could be inserted in a sealing fashion down to tube 50, and used to aspirate tissue 100 to form a dome 101. The fastener 26 could be released, and then the vacuum catheter or similar device could be withdrawn.

Although it is not illustrated, it is evident on inspection that by lengthening shell 40 and tube 50, multiple devices 26 can be stacked inside of retainer tube 40. Then, by withdrawing shell 40 a fixed distance, tissue fasteners 26 can be released one by one as required by the procedure, without having to withdraw the endoscope from the patient.

Also not illustrated is an alternate embodiment in which the tissue-piercing members 32, or their equivalent in other embodiments, project outward when in the planar state, and stabilizers 34 project inward. Referring to FIG. 6 for feature reference, stabilizers 34 located on ring 27 can be shorter, and tissue piercing elements 32 can optionally be longer. Thus, a clear space 36 in the center of the planar fastener, when closed, may be larger in this configuration.

Moreover, once the basic tissue closure mechanism illustrated in FIG. 7-10 is understood, it becomes evident that new and improved methods of endoscopic surgery are made possible by the use of the closure device of the invention. The major improvement provided by the device is the opportunity to insert an endoscopic device, carrying one or more ready-to-deploy fasteners, to a site in the body; and then, in contrast to prior art devices, to conduct procedures using instruments inserted through the endoscopic device. Because the central lumen is open, complex devices, of relatively large diameter, can be inserted. It is possible in particular to have both visualization devices and manipulative or therapeutic devices present in the endoscope lumen, with fasteners waiting to be deployed, as described in this application, at the end of the procedure.

Such procedures and devices may include, but are not limited to: vacuum, suture style attachment, needle or anchoring constructs of all types, quantity, spatial arrangement and/or delivery configuration. Multifunctional multi-lumen type devices and apparatus may include hooks, snares, barbs, needles and/or inflatable and/or vacuum element constructs whether single or multiple in nature or in combinations thereof. Any of these devices may be positioned, transported or utilized through tubes 50 and 60 of the endoscope to satisfy the surgeon's need for selective tissue position securing and management.

Furthermore it is within the scope of the preferred embodiment to envision multiple nested delivery systems and fasteners comprised of the preferred embodiment design and method, enabling the surgeon to control, manipulate access and close multiple sequential tissue membrane barriers organs, or tissues within the patient using tubes 50 and 60 as a conduit to advance to the surgical site.

Materials for Fastener Construction

In describing the embodiment of the present invention, it is preferred but not limiting to the embodiment functionality that the materials comprising the self closing tissue fastener features be selected for the ability to undergo the required deformations of stressed condition and planar condition as illustrated and defined in the numerous embodiment geometries shown by but not limited to FIGS. 1 through 6 and utilized in methods described in apparatus FIGS. 7 through 10 without mechanical failure or breakage. Preferably, loading a fastener into a delivery apparatus, thereby imparting stress or strain to the fastener 26 (or other designation), will not cause stress significant enough to permanently deform the fastener so much that it is unable to return sufficiently toward the original planar configuration to be able to fasten tissue in place. Ideally, the fastener will return to a substantially planar configuration. However, significant permanent deformation of the fastener, as well as some non-recovery due to obstruction by tissue, can be acceptable. As long as the fastener holds the tissue in place, deviations of the fastener from final planarity is acceptable. A figure of about 50% recovery is used herein as a guide to material selection, but it is to be understood that it is the functional aspect of retaining the tissue in position that is to be used to select materials, and that only simple experimentation is required to determine if a material is suitable, given that the material is known to suitable for use as a medical implant.

Alternatively, and within the scope of the invention, the degree of rotation of the tissue locking members within the embodiment required for generating appropriate tissue locking or securing effect may be varied based on the surgical application, procedure and technique employed. As such it may be advantageous to the patient for the surgeon to select an embodiment constructed from materials and geometries that may be designed to not recover completely from the stressed or annular condition, thus allowing tissue to be held in close proximity yet not in a fully compressed and/or closed state as represented or implied by the "planar" figure construct examples.

It is preferred for most embodiments of the fastener that materials selected to comprise those embodiments or portions thereof exhibit a high degree of "elasticity" and a low degree of "yield" and/or "creep". These material attributes have been shown to provide the embodiment with excellent functionality and perform in a satisfactory manner. That is, the ability of the interacting members to bend but not yield or break, while maintaining the overall geometric shape and spatial relationship, and preferably coupled with good kinetic energy storage capability, is preferred for this application. However, such high performance high strength unique materials may not necessarily be selected nor desired in specific applications where tissue high compression is not needed, and should not be construed as being a requirement of all embodiments of the present invention.

As used herein, "elasticity" refers to a material that is reversibly distortable, in that it can be bent or twisted up to 90 degrees or more, at room to body temperature, and will return to its original shape, or a reasonable approximation thereof, upon release from the "distortable" confined state Like the example of a coiled or torsion simple spring which exhibits "elasticity" and in its construct has stored energy potential which is expressed as force on its release as it return to its original condition, the composition of the preferred embodiment will return to its original shape or a reasonable approximation thereof on release from its confinement.

A "reasonable approximation" is "sufficiently close to the original configuration to reliably serve as a tissue fastener". This can readily be determined by experimentation on candidate materials—alloys, composites, laminates, and the like: Bending the proposed material through up to 90 degrees or more, and determining if the material will fasten the target tissue that it has impaled while bent, provides a simple test of suitability of a material for use in the invention.

A material suitable for use in the invention requires a sufficiently high modulus that the return force can overcome resistance by tissue; this implication is also easily tested by functional experimentation methods. The named materials in the scope of this application believed to be suitable, such as for example nitinol and certain stainless steels, have elastic moduli in the range of about 30 million psi or more. However, it is likely that not all materials with moduli in this range will be suitable. Furthermore, it may also be the case that materials, including metals, alloys, composites, laminates and/or unique combinations of materials coatings, adhesives and polymers, all or some with perhaps lower moduli, will, by their ability to be resilient and resistant to breakage when deformed, also prove to be suitable for this embodiment. Any such embodiment construct is by definition within the scope of this application In addition to simple compositions and alloys or blends of materials, composite materials and/or constructed assemblies, having interacting multiple domains and smooth junctions, can be employed as long as they meet the performance requirements. Biodegradable materials may be utilized within the construction of the self closing tissue fastener or any portions thereof. In particular, it may be advantageous for some procedures to have tissue-piercing regions of the fastener gradually degrade in situ, allowing tissue to more nearly return to its original configuration. Coatings, treatments, finishes and/or encapsulations may be utilized to further enhance the performance properties or moderate or enhance desired geometric or performance traits to met specific clinical outcomes.

The present invention may consist wholly or in part of the following types and general classes of materials: Nitinol, Stainless Steel, Spring Steel; Thermoplastic, Elastomeric and/or Thermoset Polymers or Polymer Blends; and any combinations or composite constructs combining any of these materials. It is necessary that the material have a sufficiently high modulus that the return force can overcome resistance by tissue; this is easily tested by simple experimentation. Some named materials above that are believed to be suitable, such as for example nitinol and certain stainless steels, have elastic moduli in the range of about 30 million psi or more. These materials are presently preferred. However, it is likely that not all materials with moduli in this range will be suitable. Furthermore, it may also be the case that materials, including metals, alloys, composites, laminates or unique combinations of materials coatings and adhesives, all or some with perhaps lower moduli, will, by their ability to be resilient and resistant to breakage when deformed, also prove to be suitable for this embodiment. Any such embodiment construct is by definition within the scope of this application.

Biological, drug, therapeutic and/or antibacterial coatings may also be employed on the surfaces or integral to the whole or a portion of the self closing tissue fastener and/or elements of the position and deploy apparatus to aid and assist in the healing processes or to provide and execute a specific therapeutic regimen protocol.

Photographs of actual device performance are shown in U.S. Provisional Patent Application 60/785,830, which should become available upon publication of the present application.

Various embodiments and figures have been described in this specification to allow it to be understood by persons of ordinary skill in the appropriate arts. The scope of the invention is not limited to the specific embodiments described, but is limited only by the scope of the claims.

The invention claimed is:

1. A device for fastening tissue, wherein the device comprises:
 a single closed ring having an essentially planar configuration and an essentially cylindrical configuration, wherein the ring is elastically deformable and is changed from the essentially planar configuration to the essentially cylindrical configuration by application of torsional energy, the ring having one or more tissue engaging projections and being formed of multiple functional zones each extending along part of the circumference of the ring, the functional zones comprising:
 a) a plurality of twistable zones, each of the twistable zones being capable of sustaining a 90 degree or more torsional rotation;
 b) one or more central zones resistant to deformation under torque, each tissue engaging projection extending from a central zone, each central zone including a central spine having a tissue-engaging projection and a stabilizing projection, each central zone being connected to a pair of the twistable zones at the central spine by way of central zone junctions, and the tissue-engaging projection projecting from one side of the ring along an axis parallel to the central axis of the ring when in the essentially cylindrical configuration, and the stabilizing projection projecting from an opposite side of the ring along the axis parallel to the central axis of the ring when in the essentially cylindrical configuration, each stabilizing projection extending beyond any interconnection to a twistable zone; and
 c) one or more interconnecting zones, each interconnecting zone being connected to a pair of the twistable zones and being radially displaced from the central zone junctions in the planar configuration and axially displaced from the central zone junctions in the cylindrical configuration;
 wherein reorientation of each tissue-engaging projection of the device to engage tissue, from the essentially cylindrical configuration of the ring to the essentially planar configuration, is driven by torsional energy stored in the ring.

2. The device of claim 1 wherein the one or more interconnecting zones include a material that is the same as a material of one of the twistable zones and central zones.

3. The device of claim 1 wherein the device is made from a material capable of sustaining a 90 degree or more torsional rotation, at two or more sites in the ring.

4. The device of claim 1 wherein the device further has the property that a torsional rotation of up to 90 degrees or more is substantially reversible upon reorientation of the tissue-engaging projections of the device from the essentially cylindrical configuration to the essentially planar configuration.

5. The device of claim 1 wherein the device further has the property that a torsional rotation of 90 degrees or more is capable of being reversed at least about 45 degrees.

6. The device of claim 1 wherein the device is configured to be torsionally deformed from the essentially planar configuration to the essentially cylindrical configuration by being forced onto a mandrel with an outer circumference that is in the range of about 90% to about 105% of the inner circumference of the ring of the device.

7. The device of claim 1 wherein the device is configured to be torsionally deformed from the essentially planar configuration to the essentially cylindrical configuration by forcing the stabilizing projections that project outward from the ring in the essentially planar configuration towards each other until the device converts from the essentially planar configuration to the essentially cylindrical configuration.

8. The device of claim 1 wherein the stabilizing projections are configured to hold the device stably in the essentially cylindrical configuration on the inside of a tube without additional restraints, the inside circumference of the tube being in the range of about 95% to about 120% of the outside circumference of the device in the essentially cylindrical configuration.

9. The device of claim 1 wherein the device is made at least in part from materials selected from the group consisting of stainless steel, INCONEL, Nitinol, Monel, HASTELLOY, ELGILOY, tungsten, titanium, and alloys, mixtures, laminates, composites and combinations thereof.

10. The device of claim 1, wherein at least the twistable zones include super-elastic materials.

11. The device of claim 1, wherein each tissue-engaging projection includes a tissue stop member protruding from the tissue-engaging projection for imparting a compression force to tissue engaged by the tissue-engaging projection.

12. The device of claim 1, wherein each interconnecting zone is radially displaced inwardly from the central zone junctions in the planar configuration.

13. A device for engaging tissue comprising a closed member that is elastically deformable and defines a central space, the closed member having one or more piercing members and being formed of multiple functional zones, the functional zones comprising:
 a plurality of twistable zones, each twistable zone being capable of being twisted by 90 degrees or more such that the closed member is transformed from a relaxed state comprising a planar configuration to a torsionally strained state comprising a cylindrical configuration;
 at least one interconnecting zone between a pair of twistable zones; and
 at least one central zone between a pair of twistable zones, each piercing member extending from a central zone, each central zone being resistant to deformation under torque and including a central spine having a stabilizing element and a piercing member, each central zone being connected to the pair of twistable zones at the central spine by way of central zone junctions, the piercing member projecting from one side of the closed member and the stabilizing element projecting from an opposite side of the closed member, the piercing member being reoriented, driven by torsional energy stored in the closed member, to engage tissue when the closed member is released from the torsionally strained state, the stabilizing element extending beyond any interconnection to a twistable zone, each interconnecting zone being radially displaced from the central zone junctions in the planar configuration and axially displaced from the central zone junctions in the cylindrical configuration.

14. The device of claim 13, wherein the closed member has a shape selected from the group consisting of: a circle, an ellipse, an oval, a rectangle, a triangle, a square, and a polygon.

15. The device of claim 13, wherein, when released from the torsionally strained state, torsional energy stored in the device causes the device to substantially revert to the relaxed state.

16. The device of claim 13, wherein the twistable zones include a super-elastic material.

17. The device of claim 13, wherein, in the relaxed state, the piercing member projects into the central area.

18. The device of claim 13, further including barbs protruding from the piercing member.

19. The device of claim 13, wherein the closed member further includes a plurality of interconnecting zones and a plurality of central zones.

20. The device of claim 13, wherein the piercing member includes a tissue stop member protruding from the piercing member for imparting a compression force to tissue engaged by the piercing member.

21. The device of claim 13, wherein each interconnecting zone is radially displaced inwardly from the central zone junctions in the planar configuration.

* * * * *